(12) United States Patent
Anderson et al.

(10) Patent No.: US 10,645,917 B2
(45) Date of Patent: May 12, 2020

(54) METHOD FOR REMEDIATING DEVELOPMENTALLY DELAYED PLANTS

(71) Applicant: Deere & Company, Moline, IL (US)

(72) Inventors: Noel W. Anderson, Fargo, ND (US); Larry L. Hendrickson, Grimes, IA (US)

(73) Assignee: DEERE & COMPANY, Moline, IL (US)

( * ) Notice: Subject to any disclaimer, the term of this patent is extended or adjusted under 35 U.S.C. 154(b) by 15 days.

(21) Appl. No.: 15/799,931

(22) Filed: Oct. 31, 2017

(65) Prior Publication Data

US 2019/0124910 A1    May 2, 2019

(51) Int. Cl.
| | | |
|---|---|---|
| *A01M 21/02* | (2006.01) | |
| *A01H 1/04* | (2006.01) | |
| *A01H 1/06* | (2006.01) | |
| *A01H 3/00* | (2006.01) | |
| *A01G 7/06* | (2006.01) | |

(52) U.S. Cl.
CPC ............... *A01M 21/02* (2013.01); *A01H 1/04* (2013.01); *A01H 1/06* (2013.01); *A01H 3/00* (2013.01); *A01G 7/06* (2013.01)

(58) Field of Classification Search
CPC ............ A01M 21/02; A01H 1/04; A01H 1/06
USPC .......................................................... 701/50
See application file for complete search history.

(56) References Cited

U.S. PATENT DOCUMENTS

| | | | |
|---|---|---|---|
| 7,188,450 B2* | 3/2007 | Raun | A01C 21/007 |
| | | | 47/58.1 SC |
| 8,150,554 B2 | 4/2012 | Anderson | |
| 8,437,879 B2 | 5/2013 | Anderson | |
| 8,504,234 B2 | 8/2013 | Anderson | |
| 9,076,105 B2 | 7/2015 | Anderson | |
| 2007/0061911 A9* | 3/2007 | Zhang | C07K 14/415 |
| | | | 800/278 |
| 2014/0379228 A1* | 12/2014 | Batcheller | A01C 21/005 |
| | | | 701/50 |
| 2015/0305226 A1* | 10/2015 | Zemenchik | A01C 21/007 |
| | | | 701/50 |
| 2017/0034986 A1 | 2/2017 | Koch et al. | |

(Continued)

FOREIGN PATENT DOCUMENTS

| | | |
|---|---|---|
| DE | 19913971 A1 | 9/2000 |
| WO | 2017011595 A1 | 1/2017 |

OTHER PUBLICATIONS

Bethel, Matthew; et al. "Image-Based, Variable Rate Plant Growth Regulator Application in Cotton at Sheely Farms in California." Beltwide Cotton Conferences, Nashville, TN, Jan. 6-10, 2003. Retrieved on Oct. 31, 2017. Retrieved from the Internet: <Variable rate application of PIX to cotton http://optoknowledge.com/documents/publications/OKSI-2003-02a.pdf>.

(Continued)

*Primary Examiner* — Yazan A Soofi

(57) ABSTRACT

A method for remediating developmentally delayed plants within a field of crops using at least one work vehicle during a field operation. The method comprises identifying delayed plants within the field with a sensor on the work vehicle and generating, with a processor, location data associated with the location of the delayed plant with the field. Upon arriving at the location of the delayed plant with the work vehicle, the delayed plant is remediated.

22 Claims, 4 Drawing Sheets

(56) References Cited

U.S. PATENT DOCUMENTS

2018/0020611 A1* 1/2018 LaRowe ............... A01B 51/02
701/2

OTHER PUBLICATIONS

German Search Report issued in counterpart application No. 102018216476.2 dated Apr. 26, 2019 (12 pages).

* cited by examiner

METHOD FOR REMEDIATING DEVELOPMENTALLY DELAYED PLANTS

FIELD OF THE DISCLOSURE

The present disclosure relates generally to a method for remediating developmentally delayed crop plants within a field of growing crops.

BACKGROUND OF THE DISCLOSURE

The problem of developmentally delayed crops—for example corn plants emerging significantly later than surrounding corn plants—is well known. Delayed plants use water, nutrients, and sunlight without producing a proportional amount of grain. By remediating delayed plants, the remaining crop plants have more resources with which to be productive.

SUMMARY OF THE DISCLOSURE

According to an aspect of the present disclosure, a method is provided for remediating developmentally delayed plants within a field of crops using at least one work vehicle. The method comprises identifying delayed plants within the field with a sensor on the work vehicle and generating, with a processor, location data associated with the location of the delayed plant with the field. Upon arriving at the location of the delayed plant within the field with the work vehicle, the delayed plant is remediated.

According to another aspect of the present disclosure, a method is provided for remediating developmentally delayed plants within a field with at least one work vehicle. The method comprises identifying, with a processor, a delayed plant using agricultural data for the field; generating, with the processor, location data associated with the location of the delayed plant within the field; and storing the location data. The delayed plant may then be located during a field operation using the stored location data and a sensor on a work vehicle and, upon locating the delayed plant, remediated.

According to yet another aspect of the present disclosure, a method is provided for remediating developmentally delayed plants within a field of crops using at least one work vehicle. The method comprises identifying delayed plants within the field with a sensor on a work vehicle; determining, with a processor, a delay amount for at least one delayed plant; and comparing, with the processor, the amount of delay against at least one delay development threshold. The plant is remediated if the amount of delay relative to the at least one delay development threshold Other features and aspects will become apparent by consideration of the detailed description and accompanying drawings.

BRIEF DESCRIPTION OF THE DRAWINGS

The detailed description of the drawings refers to the accompanying figures in which.

DETAILED DESCRIPTION OF THE DRAWINGS

Figure 1:
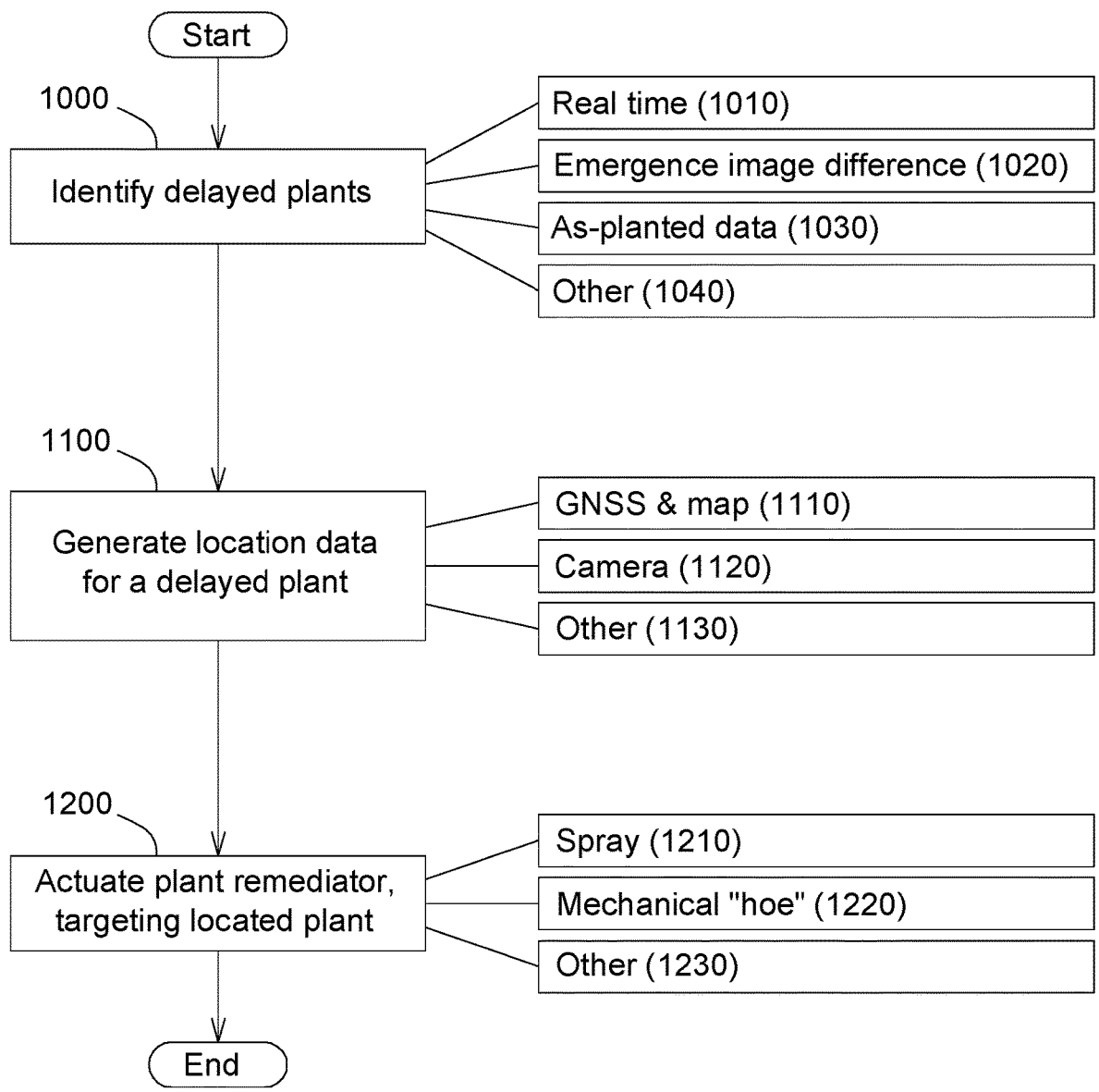
FIG. 1 is a schematic representation of a method for remediating delayed plants.

Referring now to FIG. 1, a schematic representation of a method for remediating delayed plants is shown. In Step 1000, delayed plants on a worksite (e.g., a field) are identified and data is generated associated with a single delayed plant, groups of plants or some combination thereof. The generated data may then be transmitted as a set of geographic coordinates at either or both global and local levels or other similar representation to another work vehicle or stored on a database for subsequent retrieval. This identification may occur in real time 1010, using emergence date data 1020, using as-planted data 1030, or any other suitable means 1040.

For example, as shown by Step 1100, one or more sensors mounted to a work vehicle are used to identify a delayed plant during a field operation. The work vehicle is at least one vehicle and, in one specific example, is a first work vehicle and a second work vehicle. The first and second work vehicles are typically, without limitation, any of the following: a self-propelled sprayer, a high clearance sprayer, a tractor-mounted sprayer, a tractor and towed implement such as a cultivator or fertilizer applicator, a UAV, airplane, utility vehicle, or a small terrestrial robot. The field operation may involve spraying a crop, planting, cultivating, aerial observation, crop scouting or any other operation customarily performed with a crop.

In one example, when the output of Step 1000 is agricultural data such as map having the global or local geographic coordinates of delayed plants, a Global Navigation Satellite System 1110 sensor is used to locate the work vehicle during a field operation relative to one or more delayed plants on the worksite. Location data corresponding to the location of the delayed plant is generated by a processor using the signal from sensor 1110 and, in one example, transmitted to a database or to another work vehicle.

However, when the relative plant development is being measured in real-time during a field operation as the work vehicle moves through the field, the sensor may be a camera 1120 or other suitable sensor 1130 and again location data is generated by a processor using the signal from sensors 1120 or 1130. In this example, the camera 1120 may generated an image of the delayed plant from which location data is generated. The location data of the delayed plant may be the centroid of the delayed plant derived from the image and the coordinates at which a plant remediator is actuated. In Step 1200, one or more identified delayed plants are killed by a plant remediator on the work vehicle using the data generated during the identification of the delayed plants of Step 1000. The plant remediator may be a chemical or hot liquid spray 1210, a mechanical "hoe" 1220, or any other plant killing means 1230.

Figure 2:
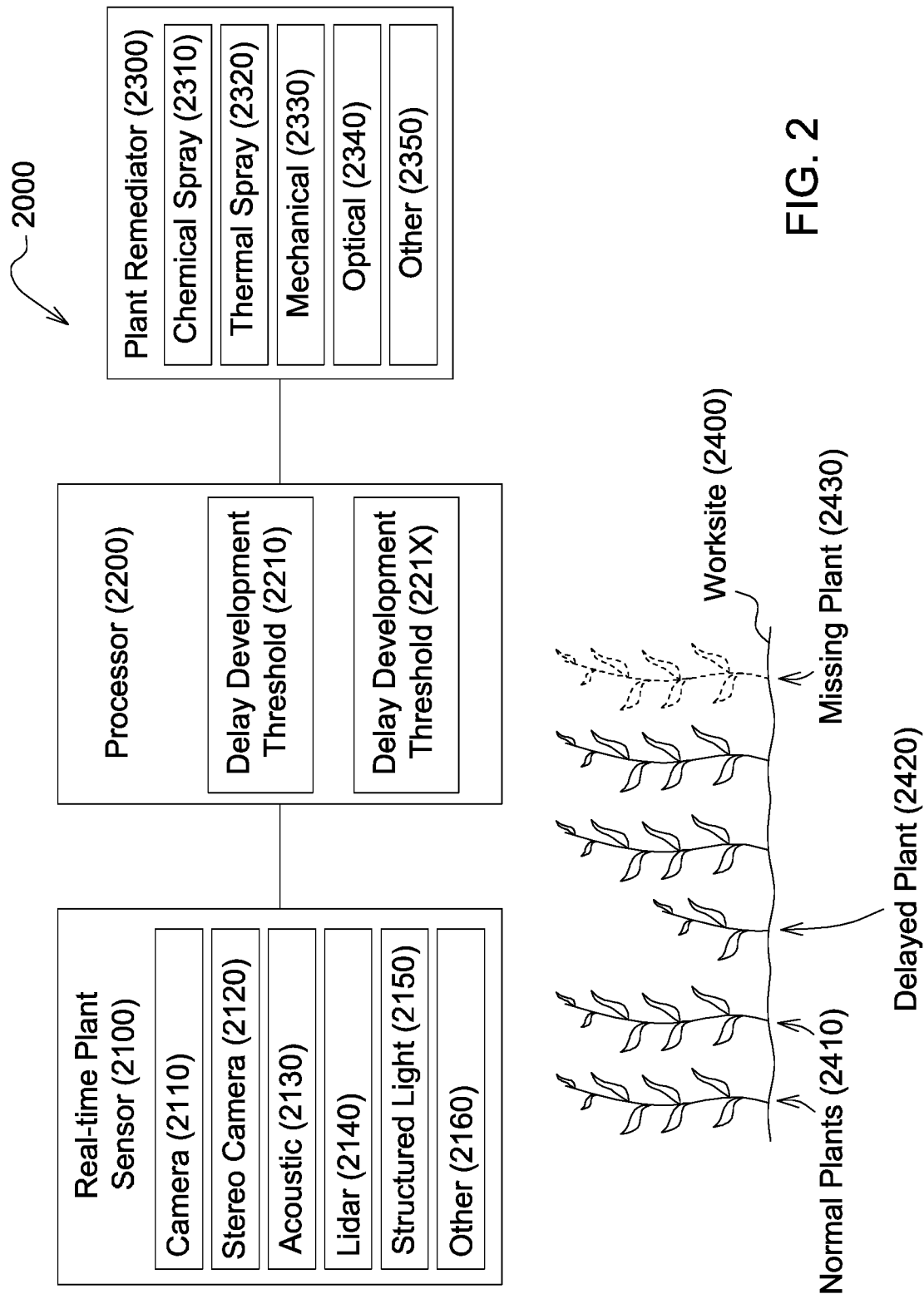
FIG. 2 is a schematic representation of a plant remediating device for remediating delayed plants.

Referring now to FIG. 2, an example embodiment 2000 which can perform the real-time method of FIG. 1 is shown. With respect to Step 1000, real-time plant sensors 2100 may include, alone or in combination, the following: camera 2110, stereo camera 2120, acoustic sensor 2130, LIDAR 2140, structured light sensor 2150, or other sensors 2160. Processor 2200 receives data about plants on a portion of worksite 2400 from real-time plant sensors 2100 and generates at least information concerning location of the delayed plants relative to the work vehicle on worksite 2400.

In another example, processor 2200 generates information concerning the amount of delay for an individual plant or a group of plants.

Developmental delay, including the amount of delay of an individual or group of plants, may be assessed on a single factor or multiple factors including, without limitation: time of emergence, growth stage, plant height, leaf count, leaf area index, plant volume, stalk diameter, shattering, lodging and reflectance spectra. Delay may be expressed in absolute terms, e.g., growth stage V4, or relative to a set of plants, e.g., $10^{th}$ percentile of emergence. Based on a delay development threshold 2210, plants are classified as normal plants 2410 or delayed plants 2420 in Step 1100. The delay development threshold may be determined manually by a user; calculated in part with user-provided agricultural data and also in part using processor 2200; or, alternatively, the threshold may be calculated and/or modeled entirely by the processor 2200 using agricultural data from one or more databases without input or with only confirmation input from the user. For example, a user may provide a delay development threshold after consulting with his or her agronomist. Alternatively, a user may provide only agricultural data in the form of an as-planted map while relying on the processor and associated real-time sensors to provide other agricultural data relating to emergence to determine the amount of delay and/or the delay development threshold.

Plants identified as being delayed or otherwise not meeting threshold 2210 are remediated by plant remediators 2300 in Step 1200. Plant remediators 2300 may include without limitation chemical sprays 2310, thermal sprays 2320 such as hot oil or liquid nitrogen, a mechanical hoe, cutter, or flail 2330, an optical means 2340 such as a laser, or any other suitable means. However, it can be appreciated by one of ordinary skill that instead of killing the delayed plant, Step 1200 may be adapted to involve plant growth stimulation using fertilizers, plant growth regulators, or soil amendments. In general, any treatment which causes a plant to grow at a faster rate than an untreated plant may be used.

In one example, stimulation may be accomplished through a foliar application of a plant growth regulator such as Ascend® SL sold by Winfield United. For example, when a delayed plant is identified, Step 1100 may generate data regarding the amount of the delay. If the amount of delay is determined to be minimal or otherwise not meet the delay development threshold 2210, the plant could be stimulated to catch up to surrounding plants or left alone entirely. In some examples, a second delay development threshold 221x may be present. If the delay fails to meet (first) delay development threshold 2210, then the plant is eliminated. If the plant exceeds (first) delay development threshold 2210 but not second delay development threshold 221x, it is stimulated. Otherwise the plant is left to continue growing as is. It can be appreciated that any number of delay development thresholds may be used to remediate—through elimination, stimulation or otherwise—a delayed plant.

In one example, the processor 2200 may be comprised of one or more of software and/or hardware in any proportion. In such an example, the processor 2200 may reside on a computer-based platform such as, for example, a server or set of servers. Any such server or servers may be a physical server(s) or a virtual machine(s) executing on another hardware platform or platforms. Any server, or for that matter any computer-based system, systems or elements described herein, will be generally characterized by one or more processors and associated processing elements and storage devices communicatively interconnected to one another by one or more busses or other communication mechanism for communicating information or data. In one example, storage within such devices may include a main memory such as, for example, a random access memory (RAM) or other dynamic storage devices, for storing information and instructions to be executed by the processor(s) and for storing temporary variables or other intermediate information during the use of the system and computing element described herein.

In one example, the processor 2200 may also include a static storage device such as, for example, read only memory (ROM), for storing static information and instructions for the processor(s). In one example, the processor 2200 may include a storage device such as, for example, a hard disk or solid state memory, for storing information and instructions. Such storing information and instructions may include, but not be limited to, instructions to compute, which may include, but not be limited to processing and analyzing agronomic data or information of all types. Such data or information may pertain to, but not be limited to, weather, soil, water, crop growth stage, pest or disease infestation data, historical data, future forecast data, economic data associated with agronomics or any other type of agronomic data or information.

In one example, the processing and analyzing of data by the processor 2200 may pertain to processing and analyzing agronomic factors obtained from externally gathered image data, and issue alerts if so required based on pre-defined acceptability parameters. RAMs, ROMs, hard disks, solid state memories, and the like, are all examples of tangible computer readable media, which may be used to store instructions which comprise processes, methods and functionalities of the present disclosure. Exemplary processes, methods and functionalities of the processor 2200 may include determining a necessity for generating and presenting alerts in accordance with examples of the present disclosure. Execution of such instructions causes the various computer-based elements of processor 2200 to perform the processes, methods, functionalities, operations, etc., described herein. In some examples, the processor 2200 of the present disclosure may include hard-wired circuitry to be used in place of or in combination with, in any proportion, such computer-readable instructions to implement the disclosure.

Figure 3:
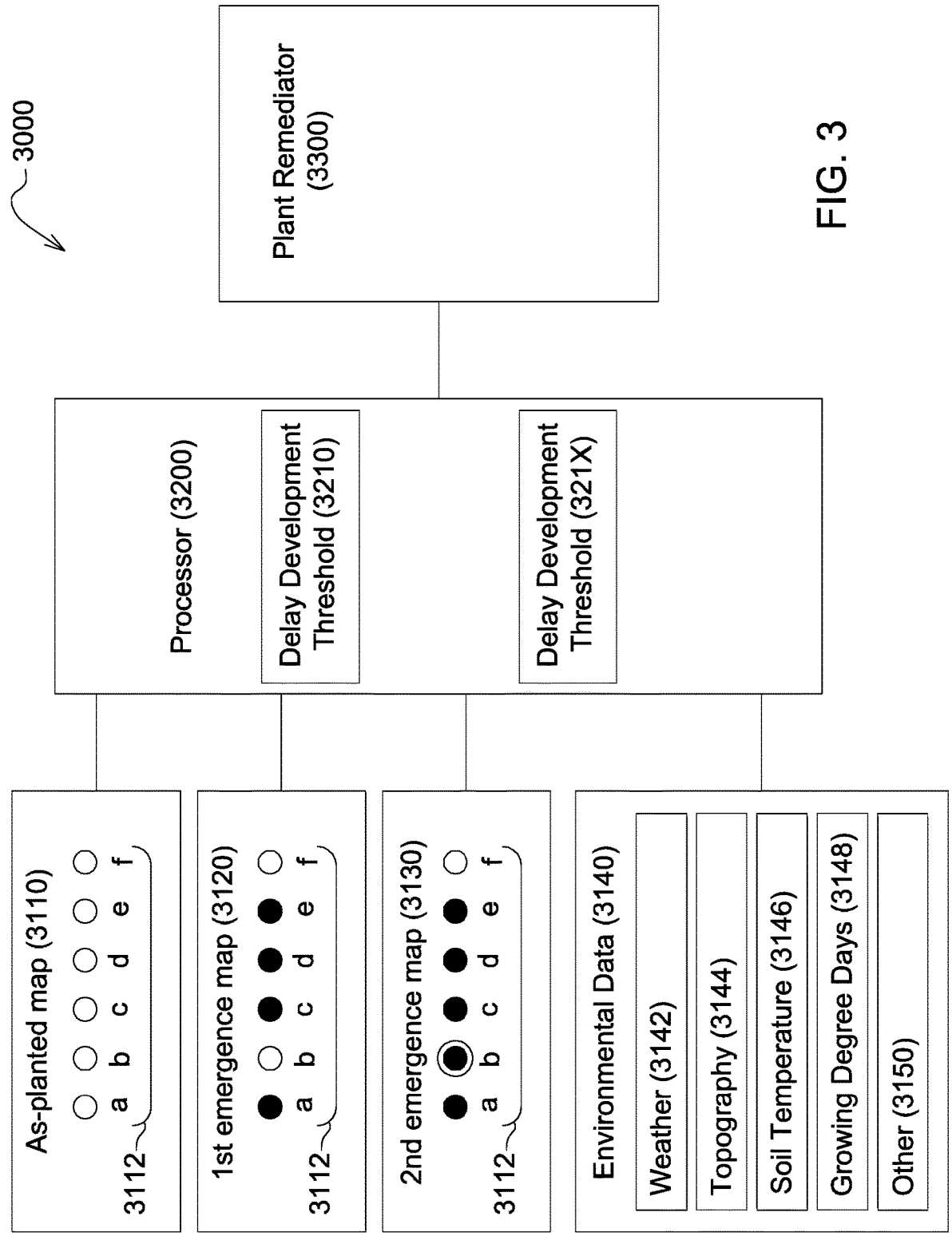
FIG. 3 is a schematic representation of a method for remediating delayed plants using at least one crop emergence map.

FIG. 3 shows an example embodiment 3000 which can perform the method of FIG. 1 using various a priori agricultural data such as planting and environmental information. The various agricultural data may be stored on a plurality of databases or database servers. In one example, the databases store a variety of planting and environmental information and additionally perform calculations and/or other functionality. Any number of databases may be included and relate to specific first agricultural data, second agricultural data or multiple sets of agricultural data. For example, agricultural data may relate to as-planted map 3110 or, alternatively, first agricultural data and second agricultural data corresponding, respectively, to a first crop emergence map 3120 and a second crop emergence map 3130 stored on the same database or different databases. Moreover, the agricultural data may have temporal differences such as, for example, a first crop emergence map acquired at a different time than the second crop emergence map using a camera mounted on a terrestrial vehicle or aerial vehicle traveling across or near worksite 2400. In some examples there are only two crop emergence maps; however, it can be appreciated that a plurality of emergence maps may be used to generate development delay data and thresholds. As mentioned above, the agricultural data may be an as-planted map 3110 acquired using planter seed location placement data generated prior to or during planting of a crop.

As-planted map 3110 shows locations of seeds or future plants 3112*a-f*. At some time after planting, the first emergence map 3120 is generated showing plants 3112*a,c,d,e* have emerged as depicted by the filled in circles. In practice, this may be based on detecting a sufficient amount of "green" at an expected seed location such as recorded in as-planted map 3110. At some time interval later, a second emergence map 3130 is generated showing that plant 3112*b* has emerged, but plant 3112*f* is still absent. This situation corresponds to FIG. 2 depicting normal plants 2410, delayed plant 2420, and missing plant 2430.

Accordingly, first emergence map 3120 and second emergence map 3130 may be collected at regular time intervals or at other intervals calculated in part with environmental data 3140 such as weather 3142, worksite topography 3144, soil temperature 3146, growing degree days 3148 or any other environmental information 3150. For example, rather than separating the intervals by time such as hours or days, the images may be separated by growing degree days 3148.

Growing degree days 3148 provides a heuristic tool useful in determining when a plant will reach various growth stages and expected water and nutrient usage. Growing degree days 3148 may account for aspects of local weather and predict a plant's pace towards maturity. Unless stressed by other agronomic factors, like moisture, the development rate from emergence to maturity for many plants may depend upon the daily air or soil temperature. For example, the growing degrees days on the sunny south side of a hill may vary from that on the less directly sunlit northern side. Growing degree days may be defined as a number of temperature degrees above a certain threshold base temperature, which varies among plant species, below which plant growth is zero or almost zero. Thus, the intervals on which to collect agricultural data, such as the first emergence map 3120 and second emergence map 3130, may be based on the accumulation of growing degree days during the vegetative states or reproductive states of the crop.

Figure 4:
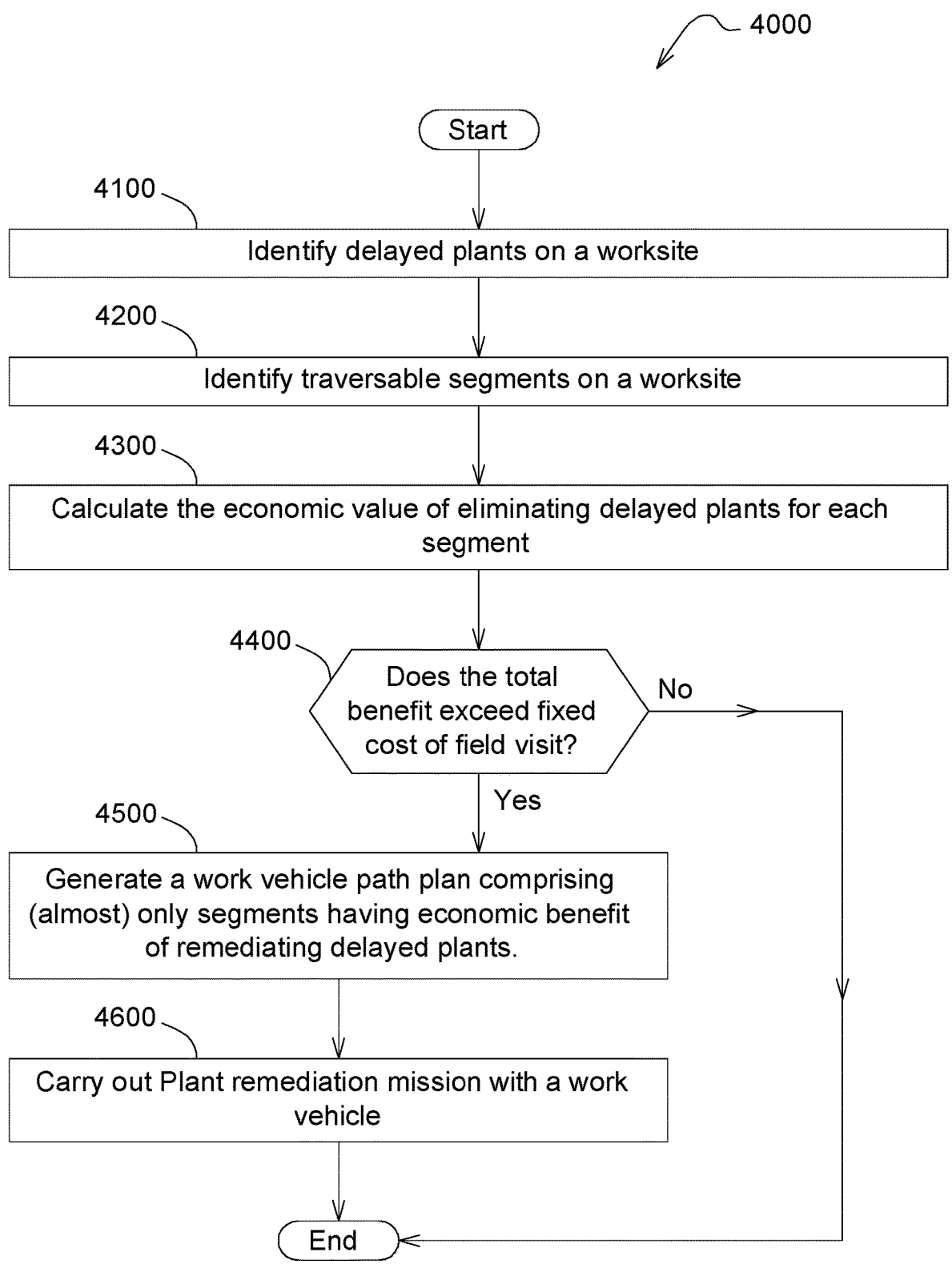
FIG. 4 is a schematic representation of a method for remediating delayed plants using economic information associated with the plant remediating activity.

It is known that significant yield loss can occur when emergence of plants within a stand are delayed. See, e.g., Ford, J. H. and D. R. Hicks. 1992, Corn growth and yield in uneven emerging stands, J. of Production Agriculture, 5:185-188; Liu, W., Tollenaar, M., Stewart, G. and Deen, W, 2004, Response of corn grain yield to spatial and temporal variability in emergence, Crop Sci. 44:847-854; and Heiniger, R. W. and L. Boerema, 2015, How important is uniform emergence in corn, In 2015, Agronomy Abstracts, ASA. The foregoing references, all of which are incorporated reference, provide guidance on establishing delay development thresholds 2210, 221*x*, 3210 and 321*x*. For example, the following limitations may be used when evaluating emergence of corn plants:

a. More than 48 hours delayed after 50% of planted seeds have emerged
b. More than 24 hours delayed after 70% of planted seeds within 5 meters have merged
c. More than 25 growing degree days after 8 adjacent plants have emerged FIG. 4 shows an example method 4000 for improving the economics of the method shown in FIG. 1 by only performing the plant remediation step 1200 in portions of worksite 2400 where the estimated benefit of the activity exceeds the cost. In Step 4100, delayed plants are identified using agricultural data acquired and stored as described with FIG. 3. Referring to Step 4200, traversable segments on worksite 2400 are identified. In a stereotypical field, this would be work vehicle passes from headland to headland. Also in stereotypical fields, these passes could be modified by waterways or other features.

Now referring to step 4300 of FIG. 4, the difference between the value of estimated benefit from remediating delayed plants and the cost of traversing the segment and remediating delayed plants is calculated for each segment. The value may be positive or negative and may be determined by relying on economic indicators or variables, either in part or in whole. For example, the values may correspond to a highest crop yield at a lowest cost. In this example, the costs are associated with a wide variety of factors, variables, and steps during the growth process. Some of the possible costs associated with the growth process include, but are not limited to, input costs from, for example, seeds, nitrogen, irrigation, pesticides, etc.; fuel charges; labor costs; etc. Additionally, the estimated benefit from remediating delayed plant may be derived from other economic factors such as, for example, expected gain in bushels per acre or plant; expected loss in bushels per acre or plant; break even costs; various cost breakdowns of inputs (e.g., nitrogen cost per pass in zone/field, cost of a unit of measure of nitrogen (e.g., pound, etc.), fuel efficiency, etc.); or a wide variety of other factors.

Further referring to FIG. 4, in Step 4400 the sum of segments with positive value is compared to fixed economic costs of treating the field such as mileage and wages to get from a starting point to the field and back. If the result is negative, then it isn't worth treating the field and the method ends. If the result is positive, or greater than a threshold value, execution proceeds to Step 4500 where the positive value segments and any necessary negative value segments are used to generate a path and treatment plan. This plan is carried out by a work vehicle in Step 4600.

In the examples of the method of FIG. 4, the steps are carried out using several candidate work vehicles such as, without limitation, a 90 foot wide self-propelled sprayer, a narrow high clearance sprayer, a narrow tractor-mounted sprayer, a UAV, or a small terrestrial robot. Each work vehicle and associated field operation has its own economics and path plan. Thus the decision is not only if a field should be treated and if so, which segments or passes, but also with which work vehicle. The work vehicle may be selected based on one or more criteria such as lowest cost, earliest mission completion (such as due to worksite accessibility, equipment availability, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the systems, methods, processes, apparatuses and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the systems, apparatuses, devices, methods and/or processes via the use of block diagrams, schematics, flowcharts, examples and/or functional language. Insofar as such block diagrams, schematics, flowcharts, examples and/or functional language contain one or more functions and/or operations, it will be understood by those within the art that each function and/or operation within such block diagrams, schematics, flowcharts, examples or functional language can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a computer readable memory medium such as a magnetic medium like a floppy disk, a hard disk drive, and magnetic tape; an optical medium like a Compact Disc (CD), a Digital Video Disk (DVD), and a Blu-ray Disc; computer memory like random access memory (RAM), flash memory, and read only memory (ROM); and a transmission type medium such as a digital and/or an analog communication medium like a fiber optic cable, a waveguide, a wired communications link, and a wireless communication link.

The herein described subject matter sometimes illustrates different components associated with, comprised of, contained within or connected with different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two or more components herein combined to achieve a particular functionality can be seen as "associated with" each other such that the desired functionality is achieved, irrespective of architectures or intermediate components. Likewise, any two or more components so associated can also be viewed as being "operably connected", or "operably coupled", to each other to achieve the desired functionality, and any two or more components capable of being so associated can also be viewed as being "operably couplable", to each other to achieve the desired functionality. Specific examples of operably couplable include, but are not limited to, physically mateable and/or physically interacting components, and/or wirelessly interactable and/or wirelessly interacting components, and/or logically interacting and/or logically interactable components.

Unless specifically stated otherwise or as apparent from the description herein, it is appreciated that throughout the present disclosure, discussions utilizing terms such as "accessing," "aggregating," "analyzing," "applying," "brokering," "calibrating," "checking," "combining," "communicating," "comparing," "conveying," "converting," "correlating," "creating," "defining," "deriving," "detecting," "disabling," "determining," "enabling," "estimating," "filtering," "finding," "generating," "identifying," "incorporating," "initiating," "locating," "modifying," "obtaining," "outputting," "predicting," "receiving," "reporting," "retrieving," "sending," "sensing," "storing," "transforming," "updating," "using," "validating," or the like, or other conjugation forms of these terms and like terms, refer to the actions and processes of a computer system or computing element (or portion thereof) such as, but not limited to, one or more or some combination of: a visual organizer system, a request generator, an Internet coupled computing device, a computer server, etc. In one example, the computer system and/or the computing element may manipulate and transform information and/or data represented as physical (electronic) quantities within the computer system's and/or computing element's processor(s), register(s), and/or memory (ies) into other data similarly represented as physical quantities within the computer system's and/or computing element's memory(ies), register(s) and/or other such information storage, processing, transmission, and/or display components of the computer system(s), computing element (s) and/or other electronic computing device(s). Under the direction of computer-readable instructions, the computer system(s) and/or computing element(s) may carry out operations of one or more of the processes, methods and/or functionalities of the present disclosure.

Those skilled in the art will recognize that it is common within the art to implement apparatuses and/or devices and/or processes and/or systems in the fashion(s) set forth herein, and thereafter use engineering and/or business practices to integrate such implemented apparatuses and/or devices and/or processes and/or systems into more comprehensive apparatuses and/or devices and/or processes and/or systems. That is, at least a portion of the apparatuses and/or devices and/or processes and/or systems described herein can be integrated into comprehensive apparatuses and/or devices and/or processes and/or systems via a reasonable amount of experimentation.

Although the present disclosure has been described in terms of specific embodiments and applications, persons skilled in the art can, in light of this teaching, generate additional embodiments without exceeding the scope or departing from the spirit of the present disclosure described herein. Accordingly, it is to be understood that the drawings and description in this disclosure are proffered to facilitate comprehension of the present disclosure, and should not be construed to limit the scope thereof.

What is claimed is:

1. A method of eliminating developmentally delayed plants within a field of crops using at least one work vehicle during a field operation, the method comprising:

identifying delayed plants within the field in response to information from a sensor on the work vehicle;

generating, with a processor, location data corresponding to a location of the delayed plant; and upon arriving at the location of the delayed plant with the work vehicle, eliminating the delayed plant.

2. The method of claim 1 further comprising:

communicating the location data to a different work vehicle; and upon arriving at the location of the delayed plant with the different work vehicle, eliminating the delayed plant.

3. The method of claim 1 wherein eliminating the delayed plant comprises actuating a plant remediator during a subsequent field operation with a different work vehicle.

4. The method of claim 2 wherein the work vehicles comprise at least one of a self-propelled sprayer, a tractor, a towed implement, a utility vehicle, a UAV, or a terrestrial robot.

5. The method of claim 1 wherein the location data is at least one of a local geographic coordinate or a global geographic coordinate associated with one or more delayed plants.

6. The method of claim 2 wherein eliminating the delayed plant involves at least one of a chemical spray, thermal spray, mechanical hoe, cutter, flail, or laser as a plant remediator.

7. The method of claim 1 further comprising:

determining, with the processor, an amount of delay of the delayed plant; and comparing, with the processor, the amount of delay against at least one delay development threshold.

8. The method of claim 7 further comprising eliminating the delayed plant if the amount of delay does not meet the delay development threshold.

9. The method of claim 1 wherein the sensor is at least one of a GPS sensor, camera, a stereo camera, an acoustic sensor, LIDAR or a structured light sensor.

10. A method of eliminating developmentally delayed plants within a field with at least one work vehicle comprising:

locating during a field operation an identified delayed plant using stored location data and a sensor on a work vehicle, the stored location data associated with the location of the delayed plant within the field identified using agricultural data; and upon locating the delayed plant, eliminating the delayed plant.

11. The method of claim 10 further comprising retrieving from a database the agricultural data.

12. The method of claim 11 wherein the agricultural data is at least one of an as-planted map, a first crop emergence map or a second crop emergence map for the field.

13. The method of claim 10 further comprising identifying, with a processor, the delayed plant prior to the field operation.

14. The method of claim 10 further comprising locating the delayed plant using the stored location data and real-time sensor data during the field operation.

15. A method of eliminating developmentally delayed plants within a field of crops using at least one work vehicle work vehicle, the method comprising:

identifying delayed plants within the field with a sensor on a work vehicle;

determining, with a processor, a delay amount for at least one delayed plant;

comparing, with the processor, the delay amount against at least one delay development threshold; and when the delay amount does not meet the delay development threshold, identifying, with the processor, the delayed plant to be eliminated.

16. The method of claim 15 wherein the delay amount is at least one of a number of hours after a portion of plants within the field have emerged or growing degree days after a portion of plants within the field have emerged.

17. The method of claim 15 further comprising the steps of:

calculating, with the processor, a cost of eliminating the delayed plant;

calculating, with the processor an expected benefit of eliminating the delayed plant; and if the expected benefit exceeds the cost, eliminating the delayed plant.

18. The method of claim 17 wherein calculating the expected benefit is determined using a change in crop yield for the field after eliminating the delayed plant.

19. The method of claim 15 further comprising the steps of:

comparing, with the processor, the delay amount against at a first delay development threshold and a second delay development threshold;

eliminating the delayed plant if the delay amount does not meet the first delay development threshold; and stimulating the delayed plant if the delay amount meets the first delay development threshold but does not meet the second delay development threshold.

20. A method of remediating developmentally delayed plants within a field of crops using at least one work vehicle during a field operation, the method comprising:

identifying delayed plants within the field with a sensor on the work vehicle;

generating, with a processor, location data corresponding to a location of the delayed plant;

determining, with the processor, a delay amount of the delayed plant;

comparing, with the processor, the delay amount against at least one delay development threshold; and upon arriving at the location of the delayed plant with the work vehicle, eliminating the delayed plant if the delay amount does not meet the delay development threshold.

21. A method of remediating developmentally delayed plants within a field of crops using at least one work vehicle work vehicle, the method comprising:

identifying delayed plants within the field with a sensor on a work vehicle;

determining, with a processor, a delay amount for at least one delayed plant;

comparing, with the processor, the delay amount against at least one delay development threshold;

calculating, with the processor, a cost of remediating the delayed plant;

calculating, with the processor an expected benefit of remediating the delayed plant; and if at least one of (1) an expected benefit exceeds a cost or (2) the delay amount does not meet the delay development threshold, remediating the delayed plant.

22. A method of remediating developmentally delayed plants within a field of crops using at least one work vehicle work vehicle, the method comprising:

identifying delayed plants within the field with a sensor on a work vehicle;

determining, with a processor, a delay amount for at least one delayed plant;

comparing, with the processor, the delay amount against at a first delay development threshold and a second delay development threshold;
eliminating the delayed plant if the delay amount does not meet the first delay development threshold; and
stimulating the delayed plant if the delay amount meets the first delay development threshold but does not meet the second delay development threshold.

* * * * *